US012715897B2

(12) United States Patent
Singh et al.

(10) Patent No.: US 12,715,897 B2
(45) Date of Patent: Aug. 25, 2026

(54) INHIBITORS OF HUMAN EPIDIDYMUS PROTEIN 4

(71) Applicant: University of Rochester, Rochester, NY (US)

(72) Inventors: Rakesh Singh, Rochester, NY (US); Richard Moore, Rochester, NY (US); Kyu Kwang Kim, Rochester, NY (US)

(73) Assignee: University of Rochester, Rochester, NY (US)

( * ) Notice: Subject to any disclaimer, the term of this patent is extended or adjusted under 35 U.S.C. 154(b) by 914 days.

(21) Appl. No.: 17/920,272

(22) PCT Filed: Apr. 21, 2021

(86) PCT No.: PCT/US2021/028343
§ 371 (c)(1),
(2) Date: Oct. 20, 2022

(87) PCT Pub. No.: WO2021/216670
PCT Pub. Date: Oct. 28, 2021

(65) Prior Publication Data

US 2023/0159586 A1 May 25, 2023

Related U.S. Application Data

(60) Provisional application No. 63/013,227, filed on Apr. 21, 2020.

(51) Int. Cl.
*C07K 5/10* (2006.01)
*A61K 38/00* (2006.01)
(Continued)

(52) U.S. Cl.
CPC ................ *C07K 5/10* (2013.01); *A61P 15/00* (2018.01); *A61P 15/08* (2018.01); *A61P 35/00* (2018.01);
(Continued)

(58) Field of Classification Search
CPC .... C07K 5/10; C07K 5/06; C07K 5/08; A61P 15/00; A61P 15/08; A61P 35/00; A61P 38/00; C07D 303/46; C07D 303/32
See application file for complete search history.

(56) References Cited

U.S. PATENT DOCUMENTS 4,708,871 A 11/1987 Geysen
4,833,092 A 5/1989 Geysen
(Continued)

FOREIGN PATENT DOCUMENTS

EP 1212422 2/2007
WO 1984/003506 9/1984
(Continued)

OTHER PUBLICATIONS

Camacho, L. H., et al. "Phase 1 clinical trial of anti-CTLA4 human monoclonal antibody CP-675,206 in patients (pts) with advanced solid malignancies." Journal of Clinical Oncology 22.14_suppl (2004): 2505-2505.
(Continued)

Primary Examiner — Randall L Beane
(74) *Attorney, Agent, or Firm* — Meunier Carlin & Curfman LLC

(57) ABSTRACT

The present disclosure provides compounds of Formula I for use in the treatment of medical disorders by the inhibition of human epididymal protein 4 (HE4).

(I)

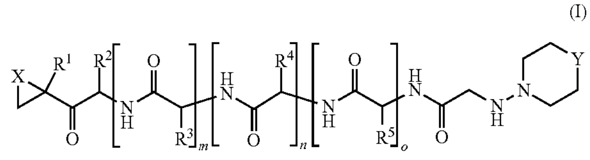

9 Claims, 2 Drawing Sheets

(51) Int. Cl.

| | |
|---|---|
| ***A61P 15/00*** | (2006.01) |
| ***A61P 15/08*** | (2006.01) |
| ***A61P 35/00*** | (2006.01) |
| ***C07D 303/46*** | (2006.01) |
| ***C07K 5/06*** | (2006.01) |
| ***C07K 5/08*** | (2006.01) |

(52) U.S. Cl.
CPC .............. *C07D 303/46* (2013.01); *C07K 5/06* (2013.01); *C07K 5/08* (2013.01); *A61K 38/00* (2013.01)

(56) References Cited

U.S. PATENT DOCUMENTS

| | | | |
|---|---|---|---|
| 5,223,409 A | 6/1993 | Ladner et al. | |
| 5,403,484 A | 4/1995 | Ladner et al. | |
| 5,556,762 A | 9/1996 | Pinilla et al. | |
| 5,571,689 A | 11/1996 | Heuckeroth et al. | |
| 5,663,143 A | 9/1997 | Ley et al. | |
| 5,750,373 A | 5/1998 | Garrard et al. | |
| 5,811,097 A | 9/1998 | Allison et al. | |
| 5,855,887 A | 1/1999 | Allison et al. | |
| 5,977,318 A | 11/1999 | Linsley et al. | |
| 6,051,227 A | 4/2000 | Allison et al. | |
| 6,207,156 B1 | 3/2001 | Kuchroo et al. | |
| 6,682,736 B1 | 1/2004 | Hanson et al. | |
| 6,984,720 B1 | 1/2006 | Korman et al. | |
| 7,109,003 B2 | 9/2006 | Hanson et al. | |
| 7,132,281 B2 | 11/2006 | Hanson et al. | |
| 7,232,818 B2 * | 6/2007 | Smyth .................. | C07K 5/1024 514/254.1 |
| 2002/0039581 A1 | 4/2002 | Carreno et al. | |
| 2002/0086014 A1 | 7/2002 | Korman et al. | |
| 2005/0201994 A1 | 9/2005 | Korman et al. | |
| 2011/0236428 A1 * | 9/2011 | Kirk ..................... | A61K 31/337 514/19.5 |
| 2014/0348854 A1 | 11/2014 | Moore et al. | |

FOREIGN PATENT DOCUMENTS

| | | |
|---|---|---|
| WO | 1984/003564 | 9/1984 |
| WO | 1998/042752 | 10/1998 |
| WO | 2000/037504 | 6/2000 |
| WO | 2001/014424 | 3/2001 |
| WO | 2004/035607 | 4/2004 |
| WO | 2007/081767 | 7/2007 |
| WO | 2007/081768 | 7/2007 |
| WO | 2010/048298 A1 | 4/2010 |
| WO | 2014/152134 A1 | 9/2014 |
| WO | 2016/154629 A1 | 9/2016 |

OTHER PUBLICATIONS

Charbonneau, Bridget, et al. "The immune system in the pathogenesis of ovarian cancer." Critical Reviews™ in Immunology 33.2 (2013) 137-164.

Clarke, B., et al. "Van de RM, Turbin D, Kalloger S, Han G, Ceballos K, Cadungog MG, et al: Intraepithelial T cells and prognosis in ovarian carcinoma: novel associations with stage, tumor type, and BRCA1 loss." Mod Pathol 22 (2009): 393-402.

Clauss, Adam, Hans Lilja, and Åke Lundwall. "A locus on human chromosome 20 contains several genes expressing protease inhibitor domains with homology to whey acidic protein." Biochemical Journal 368.1 (2002): 233-242.

Clemente, Claudio G., et al. "Prognostic value of tumor infiltrating lymphocytes in the vertical growth phase of primary cutaneous melanoma." Cancer: Interdisciplinary International Journal of the American Cancer Society 77.7 (1996): 1303-1310.

Cwirla, Steven E., et al. "Peptides on phage: a vast library of peptides for identifying ligands." Proceedings of the National Academy of Sciences 87.16 (1990): 6378-6382.

Drapkin, Ronny, et al. "Human epididymis protein 4 (HE4) is a secreted glycoprotein that is overexpressed by serous and endometrioid ovarian carcinomas." Cancer research 65.6 (2005): 2162-2169.

Gilks, C. Blake, et al. "Distinction between serous tumors of low malignant potential and serous carcinomas based on global mRNA expression profiling." Gynecologic oncology 96.3 (2005): 684-694.

Hamanishi, Junzo, et al. "Programmed cell death 1 ligand 1 and tumor-infiltrating CD8+ T lymphocytes are prognostic factors of human ovarian cancer." Proceedings of the National Academy of Sciences 104.9 (2007): 3360-3365.

Hough, Colleen D., et al. "Large-scale serial analysis of gene expression reveals genes differentially expressed in ovarian cancer." Cancer Research 60.22 (2000): 6281-6287.

Hurwitz, Arthur A., et al. "CTLA-4 blockade synergizes with tumor-derived granulocyte-macrophage colony-stimulating factor for treatment of an experimental mammary carcinoma." Proceedings of the National Academy of Sciences 95.17 (1998): 10067-10071.

Hwang, Wei-Ting, et al. "Prognostic significance of tumor-infiltrating T cells in ovarian cancer: a meta-analysis." Gynecologic oncology 124.2 (2012): 192-198.

Kirchhoff, Christiane, et al. "A major human epididymis-specific cDNA encodes a protein with sequence homology to extracellular proteinase inhibitors." Biology of reproduction 45.2 (1991): 350-357.

Köhler, Georges, and Cesar Milstein. "Continuous cultures of fused cells secreting antibody of predefined specificity." nature 256.5517 (1975): 495-497.

Koshkin, Alexei A., et al. "LNA (Locked Nucleic Acids): Synthesis of the adenine, cytosine, guanine, 5-methylcytosine, thymine and uracil bicyclonucleoside monomers, oligomerisation, and unprecedented nucleic acid recognition." tetrahedron 54.14 (1998): 3607-3630.

Lowman, Henry B., et al. "Selecting high-affinity binding proteins by monovalent phage display." Biochemistry 30.45 (1991): 10832-10838.

Mokyr, Margalit B., et al. "Realization of the therapeutic potential of CTLA-4 blockade in low-dose chemotherapy-treated tumor-bearing mice." Cancer research 58.23 (1998): 5301-5304.

Moore, Richard G., et al. "A novel multiple marker bioassay utilizing HE4 and CA125 for the prediction of ovarian cancer in patients with a pelvic mass." Gynecologic oncology 112.1 (2009): 40-46.

Moore, Richard G., et al. "Utility of a novel serum tumor biomarker HE4 in patients with endometrioid adenocarcinoma of the uterus." Gynecologic oncology 110.2 (2008): 196-201.

Mullard, Asher. "New checkpoint inhibitors ride the immunotherapy tsunami." Nature reviews Drug discovery 12.7 (2013): 489-493.

Sato, Eiichi, et al. "Intraepithelial CD8+ tumor-infiltrating lymphocytes and a high CD8+/regulatory T cell ratio are associated with favorable prognosis in ovarian cancer." Proceedings of the National Academy of Sciences 102.51 (2005): 18538-18543.

Schumacher, Karin, et al. "Prognostic significance of activated CD8+ T cell infiltrations within esophageal carcinomas." Cancer research 61.10 (2001): 3932-3936.

Wands, Jack R., and Vincent R. Zurawski Jr. "High affinity monoclonal antibodies to hepatitis B surface antigen (HBsAg) produced by somatic cell hybrids." Gastroenterology 80.2 (1981): 225-232.

Wang, Kai, et al. "Monitoring gene expression profile changes in ovarian carcinomas using cDNA microarray." Gene 229.1-2 (1999): 101-108.

Zhang, Lin, et al. "Intratumoral T cells, recurrence, and survival in epithelial ovarian cancer." New England journal of medicine 348.3 (2003): 203-213.

Office Action received in corresponding Japanese Application No. 2022-563352, mailed Jun. 3, 2025.

International Search Report and Written Opinion received in PCT/US2021/028343 dated Jul. 29, 2021, 11 pages.

* cited by examiner

INHIBITORS OF HUMAN EPIDIDYMUS PROTEIN 4

CROSS REFERENCE TO RELATED APPLICATIONS

This application is a United States National Phase Patent Application of International Patent Application Number PCT/US2021/028343, filed Apr. 21, 2021, which claims the benefit of priority to U.S. Provisional Patent Application No. 63/013,227, filed Apr. 21, 2020, the disclosures of which are incorporated herein in in their entirety.

TECHNICAL FIELD

This disclosure relates to compounds for the treatment of medical disorders, and more particularly to compounds that inhibit human epididymis protein 4 (HE4).

BACKGROUND

Human epididymis protein 4 (HE4) was identified in the epithelium of the distal epididymis using Northern blot analysis and in situ transcript hybridization (Kirchhoff et al., 1991 Biol Reprod, 45:350-357). Subsequent studies using RNA dot blots, reverse transcription polymerase chain reaction (RT-PCR) and Northern blot analysis suggested that HE4 RNA expression is widespread (Clauss et al, 2002 Biochem J, 368:233-242). Previous studies using comparative genomic hybridization and in silico chromosomal clustering reported that human chromosome 20q12-13.2 is consistently amplified in ovarian carcinomas and harbors genes that may play causal roles in the pathogenesis of the disease. This region contains a cluster of 14 genes with homology to whey acidic protein (WAP). Among these genes is HE4 that is overexpressed in ovarian and endometrial cancers and certain forms of breast cancer. The expression of HE4 protein is highly restricted in normal human tissues and is largely limited to the epithelium of the reproductive tracts to the respiratory epithelium of the proximal airways. In malignant neoplasms, gene expression profiling has consistently identified up-regulation of HE4 in carcinoma of the ovary (Wang et al, 1999 Gene, 229:101-108; Hough C D et al, 2000 Cancer Res, 60:6281-6287; Gilks C B et al., 2005 Gynecol Oncol, 96:684-694).

In malignant tumor tissues, HE4 is considered a biomarker for epithelial ovarian carcinoma (WO 2007/081768; WO 2007/081767; Moore R G et al, 2008 Gynecologic Oncology, 1 10:196-201; Moore R G et al., 2009 Gynecologic Oncology 1 12:40-46). Similarly, malignancies of corpus uteri are also positive for HE4 (Drapkin R et al, 2005 Cancer Res, 65:2162-2169). HE4 is also a marker for other Mullerian-derived tumors. In cell line studies, secreted HE4 was also seen in ovarian or endometrial cancer cell lines that express endogenous HE4 RNA (e.g., CaOV-3, ECC-1, OVCAR-3 and OVCAR5). Intracellular immunofluorescence studies revealed that HE4 is distributed on the cell surface and in a region of the cytoplasm such as the endoplasmic reticulum or the Golgi apparatus organelles (Drapkin R et al., 2005 Cancer Res, 65:2162-2169).

More than 1.5 million new cancer cases were diagnosed in 2012, excluding carcinoma in situ and basal and squamous cell skin cancer cases which do not require reporting. There is a clear need to develop new therapies for cancer as well as other medical disorders.

SUMMARY

In accordance with the purposes of the disclosed materials and methods, as embodied and broadly described herein, the disclosed subject matter, in one aspect, relates to compounds that are inhibitors of human epididymis protein 4 (HE4) as well as their use in the treatment of medical disorders such as cancers, inflammatory disorders, or organ fibrosis.

Thus, in one aspect, a compound of Formula I is provided (I)

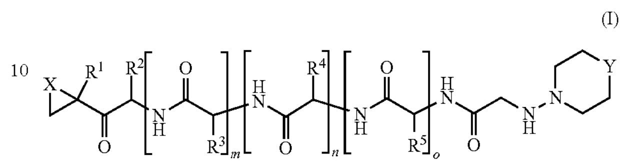

or a pharmaceutically acceptable salt or derivative thereof, wherein all variables are as defined herein.

Pharmaceutical compositions are also provided comprising a compound of Formula I, or a pharmaceutically acceptable salt or derivative thereof, in a pharmaceutically acceptable carrier.

Methods for the treatment of a medical disorder, for example such as cancer or an inflammatory disorder, are also provided comprising administering a compound of Formula I, or a pharmaceutically acceptable salt or derivative thereof. In some embodiments, the medical disorder is one which can be treated by the inhibition of HE4.

The details of one or more embodiments of the disclosure are set forth in the accompanying description below. Other features, objects, and advantages of the disclosure will be apparent from the description and drawings, and from the claims.

DESCRIPTION OF DRAWINGS

Like reference symbols in the various drawings indicate like elements.

DETAILED DESCRIPTION

Figure 1:
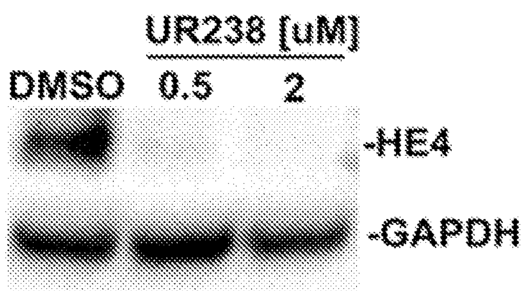
FIG. 1 shows HE4 expression levels in SKOV-3 ovarian cancer cells treated with DMSO or UR238 (0.5 or 2 μM). UR238 inhibited HE4 expression in SKOV-3 cells.

The following description of the disclosure is provided as an enable teaching of the disclosure in its best, currently known embodiments. To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are part of the present disclosure. Thus, the following description is provided as illustrative of the principles of the present disclosure and not in limitation thereof.

Definitions

Unless defined otherwise, all technical and scientific terms used herein have the same meaning as commonly understood to one of ordinary skill in the art to which this invention belongs. The following definitions are provided for the full understanding of terms used in the specification.

As used in the specification and claims, the singular form "a", "an", and "the" include plural references unless the context clearly dictates otherwise. For example, the term "an agent" includes a plurality of agents, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

Administration" to a subject includes any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or areas immediately adjacent to the point of administration and does not introduce the agent systemically in a therapeutically significant amount. For example, locally administered agents are easily detectable in the local vicinity of the point of administration but are undetectable or detectable at negligible amounts in distal parts of the subject's body. Administration includes self-administration and the administration by another.

As used here, the terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition. The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

As used herein, the terms "treating" or "treatment" of a subject includes the administration of a drug to a subject with the purpose of curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, and improvement or remediation of damage.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount". However, an appropriate "effective' amount in any subject case may be determined by one of ordinary skill in the art using routine experimentation. Also, as used herein, and unless specifically stated otherwise, an "effective amount" of a beneficial agent can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject. The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

As used herein, "pharmaceutically acceptable salt" is a derivative of the disclosed compound in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC—(CH_2)_n—COOH$ where n is 0-4, and the like, or using a different acid that produces the same counterion. Lists of additional suitable salts may be found, e.g., in Remington's Pharmaceutical Sciences, 17th ed., Mack Publishing Company, Easton, Pa., p. 1418 (1985).

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

As used herein, the term "subject" or "host" can refer to living organisms such as mammals, including, but not limited to humans, livestock, dogs, cats, and other mammals Administration of the therapeutic agents can be carried out at dosages and for periods of time effective for treatment of a subject. In some embodiments, the subject is a human.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below. As described herein, "perfluoroalkyl" is an alkyl group as described herein where each hydrogen substituent on the group has been substituted with a fluorine atom. Representative but non-limiting examples of "perfluoroalkyl" groups include trifluoromethyl, pentafluoroethyl, or heptadecafluorooctyl.

The symbols $A^n$ is used herein as merely a generic substituent in the definitions below.

The term "alkoxy" as used herein is an alkyl group bound through a single, terminal ether linkage; that is, an "alkoxy" group can be defined as —$OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This may be presumed in structural formulae herein wherein an asymmetric alkene is present, or it may be explicitly indicated by the bond symbol C═C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short-hand notation for C═O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula $—C(O)O^-$.

The term "ester" as used herein is represented by the formula $—OC(O)A^1$ or $—C(O)OA^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula $—NO_2$.

The term "cyano" as used herein is represented by the formula —CN.

The term "azido" as used herein is repreSted by the formula —$N_3$.

The term "sulfonyl" is used herein to refer to the sulfo-oxo group represented by the formula —$S(O)_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH_2$.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

COMPOUNDS

In one aspect, a compound is provided of Formula I (I)

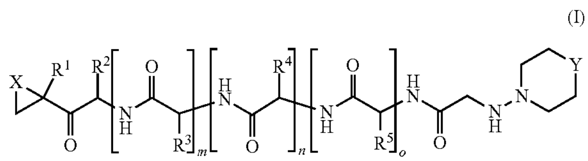

or a pharmaceutically acceptable salt or derivative thereof; wherein:

X is selected from O, —$CH_2$—, $N(R^6)$, and S;

Y is selected from S, S(=Z), and $S(=Z)_2$;

Z is selected from O, S, and $NR^7$;

m, n, and o are independently 0 or 1;

$R^1$ is H or $C_1$-$C_6$alkyl;

$R^2$, $R^3$, $R^4$, and $R^5$ are independently selected at each occurrence from H, $C_1$-$C_6$alkyl, aryl($C_0$-$C_6$alkyl), and heteroaryl($C_0$-$C_6$alkyl), each of which $R^2$, $R^3$, $R^4$, and $R^5$ may be optionally substituted with one or more substituents as defined herein;

$R^6$ is selected from H or $C_1$-$C_6$alkyl;

$R^7$ is selected from H, optionally substituted $C_1$-$C_6$alkyl, optionally substituted aryl, optionally substituted heteroaryl, —$OR^8$, and —$NR^9R^{10}$;

$R^8$ is selected from H, optionally substituted $C_1$-$C_6$alkyl, optionally substituted aryl, and optionally substituted heteroaryl; and $R^9$ and $R^{10}$ are each independently selected at each occurrence from H, optionally substituted $C_1$-$C_6$ alkyl, optionally substituted aryl, and optionally substituted heteroaryl.

In some embodiments of Formula I, X is O. In some embodiments of Formula I, X is —$CH_2$—. In some embodiments of Formula I, X is $N(R^6)$, for example NH or $N(CH_3)$. In some embodiments of Formula I, X is S.

In some embodiments of Formula I, Y is S. In some embodiments of Formula I, Y is S(=Z), for example S(=O) or $S(=NR^7)$. In some embodiments of Formula I, Y is $S(=Z)_2$, for example $S(=O)_2$ or $S(=NR^7)_2$.

In some embodiments of Formula I, m, n, and o are each 0. In some embodiments of Formula I, m and o are each 0 and n is 1. In some embodiments of Formula I, m is 0 and n and o are each 1. In some embodiments of Formula I, m is 1 and n and o are each 0. In some embodiments of Formula I, m and o are each 1 and n is 0. In some embodiments of Formula I, m and n are each 1 and o is 0. In some embodiments of Formula I, m, n, and o are each 1.

In some embodiments of Formula I, $R^1$ is hydrogen. In some embodiments of Formula I, $R^1$ is $C_1$-$C_6$alkyl, for example methyl, ethyl, n-propyl, or isopropyl. In some embodiments, $R^1$ is methyl.

In some embodiments of Formula I, $R^2$ is hydrogen. In some embodiments of Formula I, $R^2$ is $C_1$-$C_6$alkyl, for example methyl, ethyl, n-propyl, isopropyl, n-butyl, sec-butyl, or isobutyl. In some embodiments of Formula I, $R^2$ is isobutyl. In some embodiments of Formula I, $R^2$ is aryl($C_0$-$C_6$alkyl), for example phenyl, benzyl, or 2-phenylethyl. In some embodiments of Formula I, $R^2$ is benzyl. In some embodiments of Formula I, $R^2$ is 2-phenylethyl. In some embodiments of Formula I, $R^2$ is heteroaryl($C_0$-$C_6$alkyl).

In some embodiments of Formula I, $R^3$ is hydrogen. In some embodiments of Formula I, $R^3$ is $C_1$-$C_6$alkyl, for example methyl, ethyl, n-propyl, isopropyl, n-butyl, sec-butyl, or isobutyl. In some embodiments of Formula I, $R^3$ is isobutyl. In some embodiments of Formula I, $R^2$ is aryl($C_0$-$C_6$alkyl), for example phenyl, benzyl, or 2-phenylethyl. In some embodiments of Formula I, $R^3$ is benzyl. In some embodiments of Formula I, $R^3$ is 2-phenylethyl. In some embodiments of Formula I, $R^3$ is heteroaryl($C_0$-$C_6$alkyl).

In some embodiments of Formula I, $R^4$ is hydrogen. In some embodiments of Formula I, $R^4$ is $C_1$-$C_6$alkyl, for example methyl, ethyl, n-propyl, isopropyl, n-butyl, sec-butyl, or isobutyl. In some embodiments of Formula I, $R^4$ is isobutyl. In some embodiments of Formula I, $R^4$ is aryl($C_0$-$C_6$alkyl), for example phenyl, benzyl, or 2-phenylethyl. In some embodiments of Formula I, $R^4$ is benzyl. In some embodiments of Formula I, $R^4$ is 2-phenylethyl. In some embodiments of Formula I, $R^4$ is heteroaryl($C_0$-$C_6$alkyl).

In some embodiments of Formula I, $R^5$ is hydrogen. In some embodiments of Formula I, $R^5$ is $C_1$-$C_6$alkyl, for example methyl, ethyl, n-propyl, isopropyl, n-butyl, sec-butyl, or isobutyl. In some embodiments of Formula I, $R^5$ is isobutyl. In some embodiments of Formula I, $R^5$ is aryl($C_0$-

$C_6$alkyl), for example phenyl, benzyl, or 2-phenylethyl. In some embodiments of Formula I, $R^5$ is benzyl. In some embodiments of Formula I, $R^5$ is 2-phenylethyl. In some embodiments of Formula I, $R^5$ is heteroaryl($C_0$-$C_6$alkyl).

In some embodiments, the compound of Formula I is selected from a compound of Formula II (II)

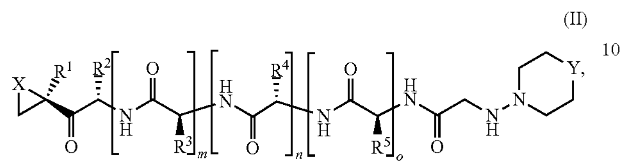

or a pharmaceutically acceptable salt or derivative thereof, wherein all variables are as defined herein.

In some embodiments, the compound of Formula I is selected from a compound of Formula III (III)

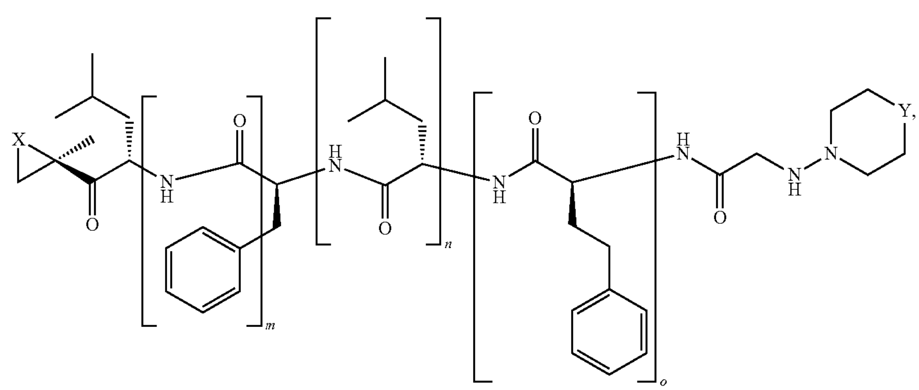

or a pharmaceutically acceptable salt or derivative thereof, wherein all variables are as defined herein.

In some embodiments, the compound of Formula I is selected from a compound of Formula Ia, Formula Ib, Formula Ic, or Formula Id:

(Ia)

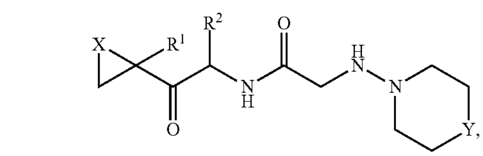

(Ib)

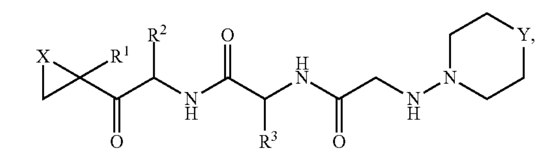

(Ic)

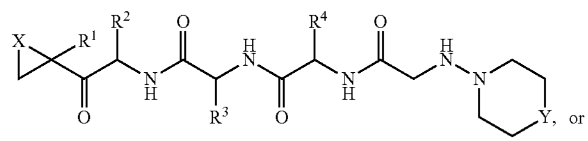

or

-continued (Id)

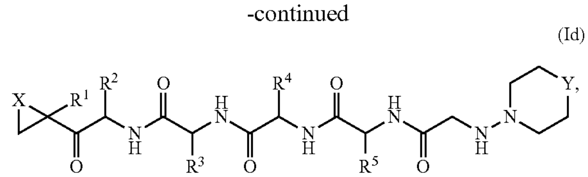

or a pharmaceutically acceptable salt or derivative thereof, wherein all variables are as defined herein.

In some embodiments, the compound of Formula I is selected from a compound of Formula IIa, Formula IIb, Formula IIc, or Formula IId:

(IIa)

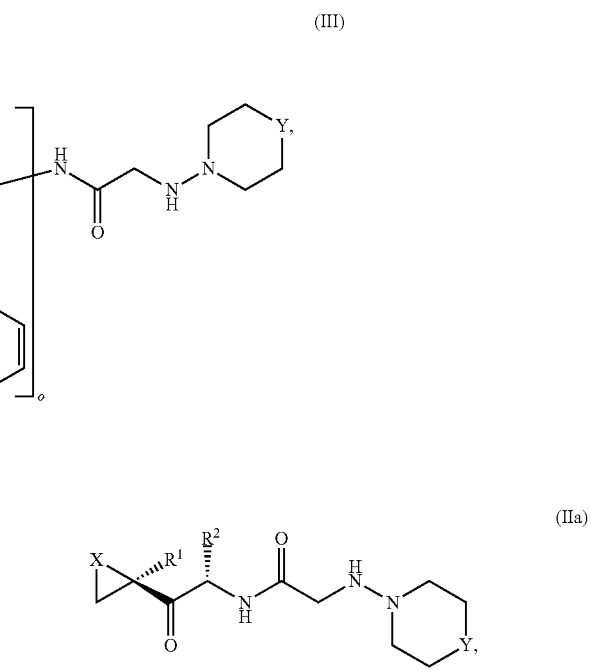

(IIb)

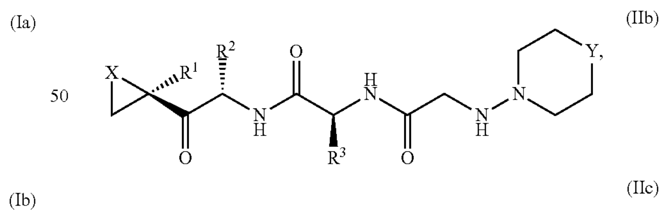

(IIc)

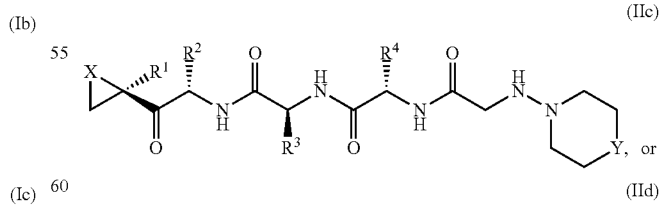

or (IId)

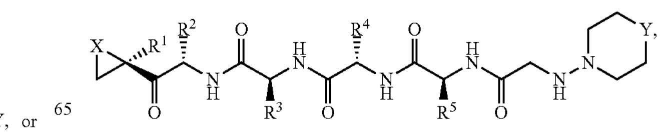

or a pharmaceutically acceptable salt or derivative thereof, wherein all variables are as defined herein.

In some embodiments, the compound of Formula I is selected from a compounds of Formula IIIa, Formula IIIb, Formula IIIc, or Formula IIId:

(IIIa)

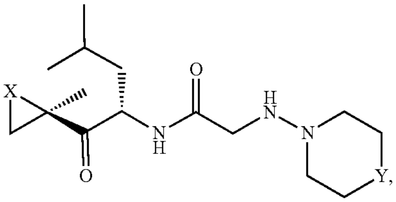

(IIIb)

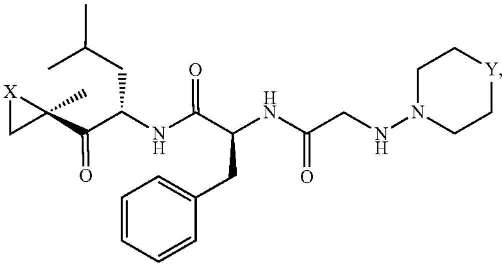

(IIIc)

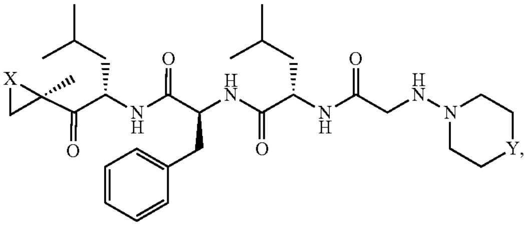

or

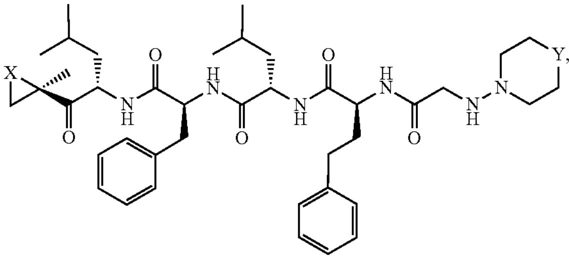

or a pharmaceutically acceptable salt or derivative thereof, wherein all variables are as defined herein.

Representative examples of compounds of Formula I include:

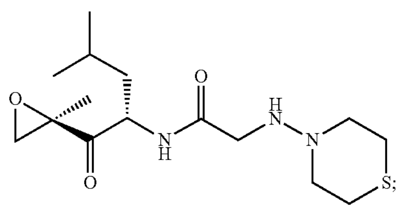

-continued

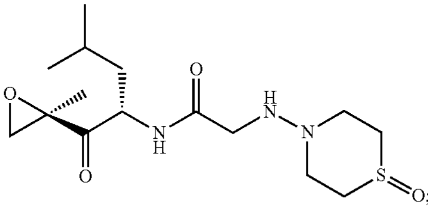

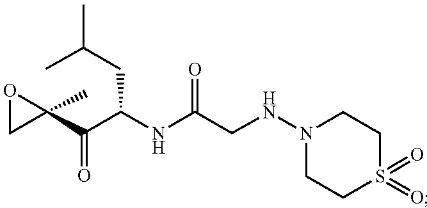

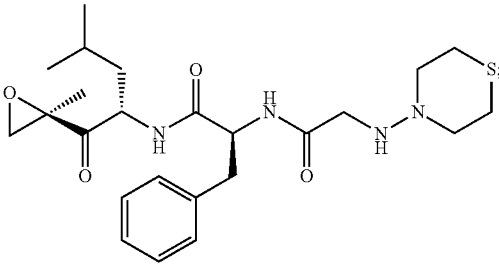

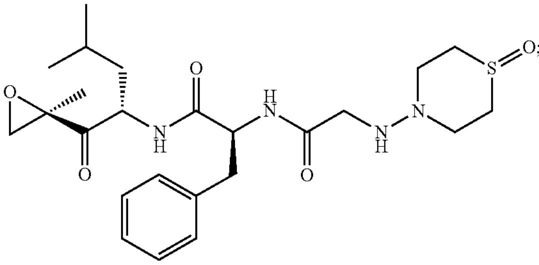

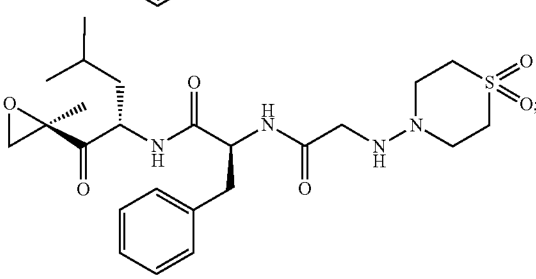

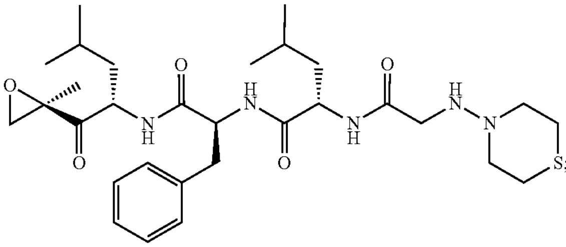

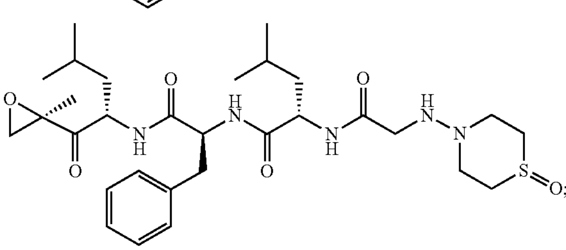

-continued

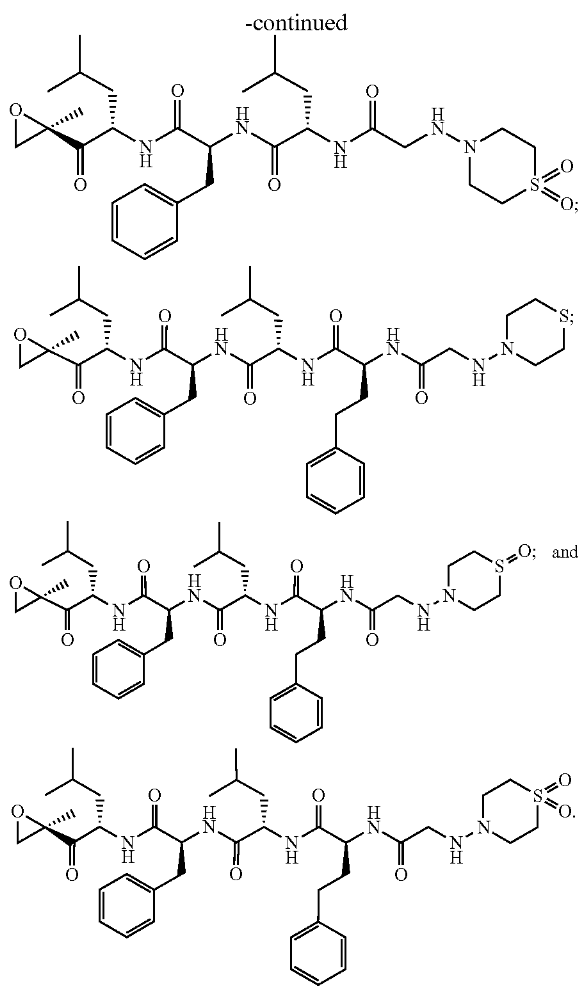

and

Methods of Treatment

Ongoing research suggests that HE4 overexpression leads to increased surface expression of PD-L1 on tumor cells and macrophages that taken together with other immune suppressive elements create an immune suppressive environment which allows tumors to escape the immune system. Further studies show that increased HE4 expression correlates with decreased CD8+ T-cell lymphocyte numbers in ovarian tumors and that targeting HE4 decreases PD-L1 expression on tumor cells both in vitro and in vivo. T-cell lymphocyte infiltration has been shown to be indicative of a host immune response to the tumor and is often correlated with a favorable prognosis (Clemente et al., 1996 Cancer, 77:1303-10; Schumacher et al., 2001 Cancer Res, 61:3932-6). In ovarian cancer, infiltration of CD3+T-lymphocytes correlates with increased progression-free and overall survival of patients Zhang et al., N Eng J Med 2003, 348:203-13). Further studies confirmed these findings and in particular that CD8+ tumor-infiltration lymphocytes correlate with more favorable prognosis and increased survival (Sato et al., Proc Natl Acad Sci USA 2005, 102:18538-43; Clarke et al., Mod Pathol 2009, 22:393-402; Hwang et al., Gyncol Oncol 2012, 124:192-8). The immune checkpoint inhibitor Programmed cell death 1 ligand 1 (PD-L1; GenBank: NP_001254635) was also noted to be prognostic in ovarian cancer (Hamanishi et al., Proc Natl Acad Sci USA 2007, 104:3360-5). It is expressed on various adaptive immune effectors in the ovarian tumor microenvironment, including CD8 and CD4 cells, where it negatively regulates cell activation. Local immune suppression is mediated by myeloid-derived dendritic cells through PD-1/PD-L1 and by generating immune suppressive mediators such as arginase, indoleamine 2,3-dioxygenase, nitric oxide and reactive oxygen species (Charbonneau et al, Crit Rev Immunol. 2013; 33(2): 137-164). In ovarian cancer, PD-1/PD-L1 is the dominant immune suppression mechanism by inhibiting anti-tumor activity of T cells. Blockade of PD-1, however, only results in partial anti-tumor effect due to release of immune regulatory cytokines, such as IL-10, IL-6, and G-CSF (Kirchhoff et al., Biol Reprod 1991, 45:350-357). The understanding of mechanisms of immune suppression is the key in being able to improve the treatment of ovarian cancer. Targeting HE4 can lead to a reduced immune suppressive tumor microenvironment and restore a host's anti-tumor immune response and, thus targeting HE4 may lead to eradication of established tumors via re-invigorating the host's immune system and/or removing the break on immune system mounted by increased PD-L1 upregulation.

Thus, in one aspect, a method for treating cancer in a subject in need thereof is provided comprising administering a therapeutically effective amount of a compound described herein to the subject, or a pharmaceutically acceptable salt or derivative thereof.

Representative cancers that can be treated using the compounds of the present disclosure include, for example, "Mullerian cancers." As used herein, the phrase "Mullerian cancer" or "Mullerian-derived tumors" indicates any cancer arising from any part of the female genital tract (such as, but not limited to, the uterus, fallopian tubes, ovaries and/or other female genital tract malignancies). In some embodiments, the term Mullerian cancer can refer to ovarian, fallopian tube, primary peritoneal, endometrial and uterine cancers, including all histologic sub types associated with the same, such as, but not limited to serous, endometrioid, clear cell, mucinous, undifferentiated, poorly differentiated, carcinosarcoma (MMMT), sarcoma germ cell tumors, and sex cord stromal tumors.

Carcinomas are cancers of epithelial origin. Carcinomas intended for treatment with the methods of this invention include, but not limited to, acinar carcinoma, acinous carcinoma, alveolar adenocarcinoma, carcinoma adenomatosum, adenocarcinoma, carcinoma of adrenal cortex, alveolar carcinoma, alveolar cell carcinoma, basal cell carcinoma, carcinoma basocellular, basaloid carcinoma, basosquamous cell carcinoma, breast carcinoma, bronchioalveolar carcinoma, bronchiolar carcinoma, cerebriform carcinoma, cholangiocellular carcinoma, chorionic carcinoma, colloid carcinoma, comedocarcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epibulbar carcinoma, epidermoid carcinoma, carcinoma epitheliate adenoids, carcinoma exulcere, carcinoma fibrosum, gelatinform carcinoma, gelatinous carcinoma, giant cell carcinoma, gigantocellulare, glandular carcinoma, granulose cell carcinoma, hair matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, lentivular carcinoma, carcinoma lenticulare, lipomatous carcinoma, lymphoepithelial carcinoma, carcinoma mastotoids, carcinoma medullare, medullary carcinoma, carcinoma melanodes, melanotonic carcinoma, mucinous carcinoma, carcinoma muciparum, carcinoma mucocullare, mucoepidermoid carcinoma, mucous carcinoma, carcinoma myxomatodes, masopharyngeal carcinoma, carcinoma nigrum, oat cell carcinoma, carcinoma ossificans, osteroid carcinoma, ovarian carcinoma, papillary carcinoma, periportal carcinoma, preinvasive carcinoma, prostate carcinoma, renal cell carcinoma of kidney, reserve cell carcinoma, carcinoma sarcomatodes, scheinderian carcinoma, scirrhous carcinoma, carcinoma scrota, signet-ring cell carcinoma, carcinoma simplex, small cell carcinoma, solandoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberrosum, tuberous carcinoma, verrucous carcinoma, carcinoma vilosum.

The invention also provides methods and agents to treat sarcomas. Sarcomas are mesenchymal neoplasms that arise in bone and soft tissues. Different types of sarcomas are recognized and these include: liposarcomas (including myxoid liposarcomas and pleomorphic liposarcomas), leiomyosarcomas, rhabdomyosarcomas, neurofibrosarcomas, malignant peripheral nerve sheath tumors, Ewing's tumors (including Ewing's sarcoma of bone, extraskeletal or non-bone) and primitive neuroectodermal tumors (PNET), synovial sarcoma, hemangioendothelioma, fibrosarcoma, desmoids tumors, dermatofibrosarcoma protuberance (DFSP), malignant fibrous histiocytoma (MFH), hemangiopericytoma, malignant mesenchymoma, alveolar soft-part sarcoma, epithelioid sarcoma, clear cell sarcoma, desmoplastic small cell tumor, gastrointestinal stromal tumor (GIST) and osteosarcoma (also known as osteogenic sarcoma) skeletal and extra-skeletal, and chondrosarcoma.

Optionally, the cancers to be treated are a refractory or a responding cancer. As used herein, a refractory cancer is a cancer that is resistant to the ordinary standards of care prescribed. These cancers, although initially responsive to treatment, recur and/or may be completely non-responsive to the treatment. This invention can also be used to treat cancers that are immunogenic. Examples of immunogenic cancers include malignant melanoma and renal cell carcinoma, Mantel cell lymphoma, follicular lymphoma, diffuse large B-cell lymphoma, T-cell acute lymphoblastic leukemia, Burkitt Lymphoma, myeloma, immunocytoma, acute promyelocyte leukemia, chronic myeloid/acute lymphoblastic leukemia, acute leukemia, B-cell acute lymphoblastic leukemia, anaplastic large cell leukemia, myelodysplasia syndrome/acute myeloid leukemia, non-Hodgkin's lymphoma, chronic lymphocytic leukemia, acute myelogenous leukemia (AML), common (pre-B)acute lymphocytic leukemia, malignant melanoma, T-cell lymphoma, leukemia, B-cell lymphoma, epithelial malignancies, lymphoid malignancies, gynecologic carcinoma, biliary adenocarcinomas and ductal adenocarcinomas of the pancreas.

The present disclosure also provides a method for inhibiting angiogenesis in a subject comprising administering a therapeutically effective amount of a compound disclosed herein, or a pharmaceutically acceptable salt or derivative thereof. Angiogenesis, the rapid proliferation of epithelial cells resulting in formation of new blood vessels, supports the progression and survival of tumors. As a secondary effect, angiogenesis may damage the various organs and tissues, eyes, skin, heart, blood vessels, lung, GI tract and genitourinary tract. Methods and techniques to assess angiogenesis are known to those of ordinary skill in the art.

Also provided are methods for suppressing tumor cell growth in a subject in need thereof comprising administering a therapeutically effective amount of a compound described herein, or a pharmaceutically acceptable salt thereof. In some embodiments, tumor cell growth is suppressed or inhibiting by inhibiting the activity of level of HE4 in the tumor cell.

Also provided are method for sensitizing a tumor to treatment with an additional therapeutic agent comprising administering a therapeutically effective amount of a compound described herein, or a pharmaceutically acceptable salt thereof.

In another aspect, methods are provided for the treatment of an inflammatory disorder in a subject in need thereof comprising administering a therapeutically effective amount of a compound disclosed herein to the subject, or a pharmaceutically acceptable salt or derivative thereof. Representative examples of inflammatory disorders include peritonitis, osteoarthritis, acute pancreatitis, chronic pancreatitis, asthma, adult respiratory distress syndrome, glomerulonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, inflammatory bowel disease, Crohn's disease, psoriasis, atopic dermatitis, graft vs. host disease, osteoporosis, multiple myeloma-related bone disorder, leukemias and related disorders, myelodysplastic syndrome, acute myelogenous leukemia, chronic myelogenous leukemia, metastatic melanoma, Kaposi's sarcoma, multiple myeloma, sepsis, septic shock, Shigellosis, Alzheimer's disease, Parkinson's disease, cerebral ischemia, myocardial ischemia, spinal muscular atrophy, multiple sclerosis, AIDS-related encephalitis, HIV-related encephalitis, aging, alopecia, neurological damage due to stroke, ulcerative colitis, infectious hepatitis, juvenile diabetes, lichen planus, acute dermatomyositis, eczema, primary cirrhosis, uveitis, Behcet's disease, atopic skin disease, pure red cell aplasia, aplastic anemia, amyotrophic lateral sclerosis, nephrotic syndrome, burns, bronchitis, tendinitis, bursitis, periarteritis nodosa, thyroiditis, Hodgkin's disease, rheumatic fever, sarcoidosis, polymyositis, gingivitis, hypersensitivity, conjunctivitis, swelling occurring after injury, allergic rhinitis, endotoxin shock syndrome, and atherosclerosis, psoriatic arthritis, vasculitis, Polymyalgia, Rheumatica, Wegener's granulomatosis, temporal arteritis, chronic obstructive pulmonary disease, cryoglobulinemia, transplant rejection and ataxia telangiectasia.

In another aspect, methods are provided for the treatment of organ fibrosis in a subject in need thereof comprising administering a therapeutically effective amount of a compound disclosed herein to the subject, or a pharmaceutically acceptable salt of derivative thereof. Representative examples of organ fibrosis which may be treated include renal fibrosis, pulmonary fibrosis, cirrhosis, endomyocardial fibrosis, Crohn's disease, liver fibrosis, heart fibrosis, scleroderma, or progressive massive fibrosis.

In another aspect, a method is provided to treat infertility in a subject in need thereof comprising administering a therapeutically effective amount of a compound described herein, or a pharmaceutically acceptable salt or derivative thereof.

Combination Therapies

The compounds as described herein may be administered in combination with other therapies such as, for example, radiation therapy, surgery, conventional chemotherapy, one or more checkpoint inhibitors, or with a combination of one or more additional therapies. The methods and agents derived from this invention may be administered alone in a pharmaceutical composition or combined with therapeutically effective and physiologically acceptable amount of one or more other active ingredients or agents. Such other active ingredient includes, but is not limited to glutathione antagonists, angiogenesis inhibitors, chemotherapeutic agent(s) and antibodies (e.g., cancer antibodies). The agents described in this invention may be administered simultaneously or sequentially. The separation in time between administrations may be minutes, hours, days or it may be longer.

For example, the compounds described herein can be administered before, after, or simultaneously with chemotherapeutic and/or cytotoxic agents such as alkylating agents (e.g., chlorambucil, cyclophosphamide, ccnu, melphalan, procarbazine, thiotepa, bcnu, and busulfan), antimetabolites (e.g., 6-mercaptopurine and 5-fluorouracil), anthracyclines (e.g., daunorubicin, doxorubicin, idarubicin, epirubicin, and mitoxantrone), antitumor antibiotics (e.g., bleomycin), monoclonal antibodies (e.g., alemtuzumab, bevacizumab, cetuximab, gemtuzumab, ibritumomab, panitumumab, rituximab, tositumomab, and trastuzumab), platinums (e.g., cisplatin, oxaliplatin, and carboplatin), plant alkaloids (e.g., vincristine), topoisomerase I or II inhibitors (e.g., irinotecan, topotecan, amsacrine, etoposide, etoposide phosphate, and teniposide), *vinca* alkaloids (e.g., vincristine, vinblastine, vinorelbine, and vindesine), taxanes (e.g., paclitaxel and docetaxel), epipodophyllotoxins (e.g., etoposide and teniposide), nucleoside analogs, and angiogenesis inhibitors (e.g., Avastin (beracizumab), a humanized monoclonal antibody specific for VEGF-A). Examples of glutathione antagonists include but are not limited to buthionine sulfoximine, cyclophosphamide, ifosphamide, actinomycin-d and N-(4-hydroxyphenyl) retinamide (4-HPR). Examples of angiogenesis inhibitors include but are not limited to 2-methoxyestradiol (2-ME), AG3340, Angiostatin, antithrombin-III, Anti-VEGF antibody, Batimastat, bevacizumab (Avastin), BMS-275291, CA1, Canstatin, combretastatin, Combretastatin-A4 phosphate, CC-5013, captopril, celecoxib, Dalteparin, EMD121974, Endostatin, Erlotinib, Gefitinib, Genistein, Halofuginone, ID 1, ID3, IM862, Imatinib mesylate, Inducible protein-10, Interferon-alpha, Interleukin-12, Lavendustin-a, LY317615, or AE-941, Marimastat, Mapsin, Medroxyprogesterone acetate, Meth-1, Meth-2, Neovastat, Osteopontin cleaved product, PEX, Pigment epithelium growth factor (PEGF), platelet growth factor 4, prolactin fragment, proliferin-related protein (PRP), PTK787/ZK222584, recombinant human platelet factor-4 (rPF4), restin, squalamine, SU5416, SU6668, Suramin, Taxol, Tecogalan, Thalidomide, Tetrathiomolybdate (TM), Thrombospondin, TNP-470, Troponin I, Vasostatin, VEGF1, VEGF-TPvAP and ZD6474. In some embodiment the angiogenesis inhibitor is a VRGF antagonist. The VEGF antagonist may be a VEGF binding molecule. VEGF binding molecule include VEGF antibodies, or antigen binding fragment (s) thereof. One example of a VEGF antagonist is NeXstar.

Chemotherapeutic agents that can be combined with the compounds disclosed herein include, but are not limited to, DNA damaging agents and these include topoisomerase inhibitors (e.g., etoposide, camptothecin, topotecan, irinotecan, teniposide, mitoxantrone), anti-microtubule agents (e.g., vincristine, vinblastine), antimetabolite agents (e.g., cytarabine, methotrexate, hydroxyurea, 5-fluorouracil, flouridine, 6-thioguanine, 6-mercaptompurine, fludarabine, pentostatin, chlorodeoxyadenosine), DNA alkylating agents (e.g., cisplatin, mecholorethamine, cyclophosphamide, ifosphamide, melphalan, chlorambucil, busulfan, thiotepa, carmustine, lomustine, carboplatin, dacarbazine, procarbazine) and DNA strand break inducing agents (e.g., bleomycin, doxorubicin, daunorubicin, idarubicin, mitomycin C).

Other chemotherapeutic agents that can be combined with the compounds described herein include: synthetic, semi-synthetic and naturally derived agents. Important chemotherapeutic agents include, but are not limited to, Avicine, Aclarubicin, Acodazole, Acronine, Adozelesin, Adriamycin, aldesleukin, Alitretinoin, AUopurinol sodium, Altretamine, Ambomycin, Ametantrone acetate, Aminoglutethimide, Amsacrine, Anastrazole, Annonaceous Acetogenins, Anthramycin, Asimicin, Asparaginase, asperlin, Azacitidine, azetepa, Azotomycin, batimastat, benzodepa, bexarotene, Bicalutamide, Bisantrene, Bisnafide, Bizelesin, Bleomycin, Brequinar, Bropirimine, Bullatacin, Busulfan, Cabergoline, cactinomycin, calusterone, caracemide, carbetimer, carboplatin, carmustine, carubicin, carzelesin, cedefingol, chlorambucil, celecoxib, cirolemycin, cisplatin, cladribine, crisnatol, cyclophosphamide, cytarabine, dacarbazine, DACA, dactinomycin, Daunorubicin, daunomycin, Decitabine, denileukin, Dexormaplatin, Dezaguanine, Diaziquone, Docetaxel, Doxorubicin, Droloxifene, Dromostalone, Duazomycin, Edatrexate, Eflornithine, Elsamitrucin, Estramustine, Etanidazole, Etoposide, Etoprine, Fadrozole, Fazarabine, Fenretinide, Floxuridine, Fludarabine, Fluorouracil, Flurocitabine, 5-FdUMP, Fosquidone, Fosteuecine, FK-317, FK-973, FR-66979, FR-900482, Gemcitabine, Gemtuzumab, Ozogamicin, Gold Aul 98, Goserelin, Guanacone, Hydroxyurea, Idarubicin, Ilmofosine, Interferon alpha and analogs, Iproplatin, irinotecan, Lanreotide, Letrozole, Leuprolide, Liarozole, Lometrexol, Lomustine, Losoxantrone, masoprocol, Maytansine, Mechlorethamine, Megestrol, Melengestrol, Melphalan, Menogaril, Metoprine, maturedepa, mitindomide, Mitocarcin, Mitogillin, Mitomalacin, Mitomycin, Mitomycin C, Mitosper, Mitotane, Mitoxantrone, Mycophenolic acid, Nocodazole, Nogalamycin, Oprelvekin, ormaplatin, Oxisuran, Paclitaxel, pamidronate, pegaspargase, Peliomycin, Pentamustine, Peplomycin, Perfosfamide, Pipobroman, Piposulfan, Piroxantrone, Plicamycin, Plomestane, Porfimer, Porfiromycin, Prednimustine, procarbazine, Puromycin, Pyrazofurin, Riboprine, Rituximab, Rogletimide, Rolliniastatin, safingol, Samarium, Semustine, Simtrazene, Sparfosate, Sparsomycin, spirogermanium, Spiromustine, Spiroplatin, Squamocin, Squamotacin, streptonigrin, streptozocin, SrC12, Sulphofenur, Talisomycin, Taxane, Toxoid, Tecoglan, Tegafur, teloxantrone, Temoporfin, teniposide, Teroxirone, Testolactone, Thiamiprine, Thiotepa, Thymitaq, Tiazofurin, Tirapazamine, Tomudex, Top-53, Topotecan, Toremixifme, Trastuzumab, Trestolone, triciribine, Triciribine, Trimetrexate, trimetrexate glucuronate, Triptorelin, Tubulozole, uracil mustard, Uredepa, valrubicin, vapreotide, Vinblastine, Vincristine, Vindesine, Vinepidine, Vinglycinate, Vinleurosine, Vinorelbine, Vinrosidine, Vinzolidine, Vorozole, Zeniplatin, Zinostatin, Zorubicin, 2-cholrodeoxyrubicine, 2'-deoxyformycin, 9-aminocamptothecin, raltitrexed, N-propargyl-5,8-didezafolic acid, 2-cholo-2'arabinofluoro-2' deoxyadenosine, 2-cholo-2'-deoxyadenosine, anisomycin, Trichostatin, hPRL-G129R, CEP-751, Linomide, Sulfur mustard, nitrogen mustard, N-methyl-N-nitrosourea, fotemustine, Streptozotocin, dacarbazine, mitozolomide, temozolomide, AZQ, ormaplatin, CI-973, DWA21 14R, JM216, JM335, Bisplatinum, Tomudex, azacitidine, cytrabincine, gemcitabine, 6-mercaptopurine, Hypoxanthine, Teniposide, CPT-1 1, Doxorubicin, Daunorubicin, Epirubicin, darubicin, losoxantrone, amsacrine, pyrazoloacridine, all trans retinol, 14-hydroxy-retro-retinol, all-trans retinoic acid, N-(4-hydroxyphenyl) retinamide, 13-cisretinoic acid, 3-methyl TTNEB, 9-cisretenoic acid, fludarabine, and 2-Cda.

Other chemotherapeutic agents that can be combined with the compounds described herein include: 20-epil,25-dihydroxyvitamin-D3, 5-ethynyl uracil, abiraterone, aclarubicin, acylfulvene, adecylpenol, adozelesin, aldesleukin, ALL-TK antagonists, altretamine, ambumastine, amidox, amifostine, amino levulinic acid, anagrelide, anastrozole, andrographolide, angiogenesis inhibitors, antagonist D, antagonists D, antarelix, anti-dorsalizing morphogenetic protein-1, antiandrogen, antiestrogen, antineoplastone, antisense oligonucleotides, aphidicolin, apoptosis gene modulators, apoptosis regulators, apurinic acid, ara-cdp-dl-PTBA, arginine aminase, asulacrine, atamestine, atrimustine, axinamastine 1 and axinamastine 2, axinamastine 3, azasetron, azatoxin, azatyrosine, baccatin III derivatives, balanol, BCR/ABL antagonist, benzochlorins, benzoylsaurosporine, beta lactam derivatives, beta-alethine. Perillyl alcohol, phenozenomyein, phenyl acetate, phosphatase inhibitors, picibanil, pilocarbine and salts or analogs thereof, pirarubucin, piritrexim, placetin A, placetin B, plasminogen activator inhibitor, platinum complex, phenyl ethyl isothiocyanate and analogs thereof, platinum compounds, platinum triamine complex, podophylotoxin, porfimer sodium, porphyromycin, propyl bis acridones, prostaglnadins J2, protease inhibitors, protein A based immune modulators, PKC inhibitors, microalgal, protein tyrosine phosphatase inhibitors, purine neucleoside phosphorylase inhibitors, purpurins, pyrazoloacridines, pyridoxylated haemoglobn polyoxyethylene conjugate, raf antagonists, raltitrexed, ramosetron, ras farnesyl protein tranaferase inhibitors, rasinhibitors, ras-GAP inhibitors, ratellitptine demethylated, Rhenium Re 186 etidronate, rhizoxine, ribozyme, RII retinide, rogletimide, rosagliatazone and analogs and derivatives thereof, rohitukine, romurtide, roquinimex, rubiginone B1, ruboxyl, safingol, saintopin, SarCNU, sarcophytol A, sargrmostim, sdi 1 mimetics, semustine, senescence derived inhibitor 1, sense oligonucleotide, signal transduction inhibitors, signal transduction modulators, single chain antigen binding protein, sizofiran, sobuzoxane, sodium borocaptate, sodium phenyl acetate, solverol, somatomedin binding protein, sonermin, sparfosic acid, spicamycin D, spiromustin, splenopentine, spongistatin 1, squalamine, stem cell inhibitor, stem cell division inhibitor, stipiamide, stromelysin, sulfinosine, superactive vasoactive intestinal peptide antagonists, suradista, siramin, swainsonine, synthetic glycosaminoglycans, tallimustine, tamoxifen methiodide, tauromustine, tazarotene, tacogalan sodium, tegafur, tellurapyrilium, telomerase inhibitors, temoporfin, tmeozolomide, teniposide, tetrachlorodecaoxide, tetrazomine, thaliblastine, thalidomide, thiocoraline, thrombopoetin and mimetics thereof, thymalfasin, thymopoetin receptor agonist, thymotrinan, thyroid stimulating harmone, tin ethyl etiopurpin, tirapazamine, titanocene and salts thereof, topotecan, topsentin, toremifene, totipotent stem cell factors, translation inhibitors, tretinoin, triacetyluridine, tricribine, trimetrexate, triptorelin, tropisetron, turosteride, tyrosine kinase inhibitors, tyrphostins, UBC inhibitors, ubenimex, urogenital sinus derived growth inhibitory factor, urokinase receptor antagonists, vapreotide, variolin B, vector system, erythrocyte gene therapy, velaresol, veramine, verdins, verteporfin, vinorelbine, vinxaltine, vitaxin, vorozol, zanoterone, zeniplatin, zilascorb and zinostatin.

Further chemotherapeutic agents that can be combined with the compounds described herein include: antiproliferative agents (e.g., piritrexim isothiocyanate), antiprostatic hypertrophy agents (sitogluside), Benign prostatic hyperplasia therapy agents (e.g., tomsulosine, RBX2258), prostate growth inhibitory agents (pentomone) and radioactive agents: Fibrinogen 11 25, fludeoxyglucose F18, Flurodopa F18, Insulin 1125, lobenguane 1123, lodipamide sodium 1131, lodoantipyrine 1131, Iodocholesterol 1131, Iodopyracet 1125, Iofetamine HCL 1123, Iomethin 1131, Iomethin 1131, Iothalamate sodium 1125, Iothalamate 1131, Iotyrosine 1131, Liothyronine 1125, Merosproprol Hgl 97, Methyl ioodobenzoguanine (MIBG-I131 or MIBGI 123), selenomethionine Se75, Technetium Tc99m furifosmin, technetium Tc99m gluceptate, Tc99m Biscisate, Tc99m disofenin, TC99m gluceptate, Tc99m lidofenin, Tc99m mebrofenin, Tc99m medronate and sodium salts thereof, Tc99m mertiatide, Tc99m oxidronate, Tc99m pentetate and salts thereof, Tc99m sestambi, Tc99m siboroxime, Tc99m succimer, Tc99m sulfur colloid, Tc 99m teboroxime, Tc 99m Tetrofosmin, Tc99m Tiatide, Thyroxine 1125, Thyroxine 1131, Tolpovidone 1131, Triolein 1125 and Treoline 1125, and Treoline 131, MIBG-I123 and MIBG 1131.

In some embodiments, the compounds described herein are administered in combination with one or more immune checkpoint inhibitors, kinase inhibitors, tubulin inhibitors, or topoisomerase inhibitors.

In some embodiments, the compounds described herein are administered in combination with one or more immune checkpoint inhibitors. Immune checkpoint inhibitors include any agent that blocks or inhibits in a statistically significant manner, the inhibitory pathways of the immune system. Illustrative immune checkpoint targets for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory CD8+ (αβ) T cells), CD160 (also referred to as BY55), CGEN-15049, CHK 1 and CHK2 kinases, A2aR and various B-7 family ligands. B7 family ligands include, but are not limited to, B7-1, B7-2, B7-DC, B7-H1, B7-H2, B7-H3, B7-H4, B7-H5, B7-H6 and B7-H7 Immune checkpoint inhibitors include antibodies, or antigen binding fragments thereof, other binding proteins, biologic therapeutics or small molecules, that bind to and block or inhibit the activity of one or more of CTLA-4, PDL1, PDL2, PD1, BTLA, HVEM, TIM3, GAL9, LAG3, VISTA, KIR, 2B4, CD160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody) and Yervoy/ipilimumab (anti-CTLA-4 checkpoint inhibitor). Checkpoint protein ligands include, but are not limited to PD-L1, PD-L2, B7-H3, B7-H4, CD28, CD86 and TIM-3.

In one embodiment, the present invention covers the compounds of the present invention may be used with one or more additional therapeutics that block the interaction between immune checkpoint receptor programmed cell death protein 1 (PD-1) and its ligand PD-L1. See A. Mullard, "New checkpoint inhibitors ride the immunotherapy tsunami," Nature Reviews: Drug Discovery (2013), 12:489-492. PD-1 is expressed on and regulates the activity of T-cells. Specifically, when PD-1 is unbound to PDL-1, the T-cells can engage and kill target cells. However, when PD-1 is bound to PDL-1 it causes the T-cells to cease engaging and killing target cells. Furthermore, unlike other checkpoints, PD-1 acts proximately such the PDLs are overexpressed directly on cancer cells which leads to increased binding to the PD-1 expressing T-cells.

In another aspect, the compounds of the present disclosure may be used in combination with antibodies that can act as agonists of PD-1 and which thereby modulate immune responses regulated by PD-1. In one embodiment, the anti-PD-1 antibodies can be antigen-binding fragments. Anti-PD-1 antibodies disclosed herein are able to bind to human PD-1 and agonize the activity of PD-1, thereby inhibiting the function of immune cells expressing PD-1. In some embodiments, the compounds of the present disclosure may be used in combination with one or more PD-1 inhibitors selected from pembrolizumab, nivolumab, cemiplimab, spartalizumab, camrelizumab, sintilimab, tislelizumab, toripalimab, nivolumab, AMP-224, or AMP-514. In some embodiments, the compounds of the present disclosure may be used in combination with one or more PD-L1 inhibitors selected from atezolizumab, avelumab, durvalumab, KNO35, CK-301, AUNP12, CA-170, or BMS-986189.

In some embodiments, the compounds of the present disclosure may be used in combination with one or more therapeutic agents that inhibit CTLA-4. Suitable anti-CTLA4 antagonist agents for use herein, include, without limitation, anti-CTLA4 antibodies, human anti-CTLA4 antibodies, mouse anti-CTLA4 antibodies, mammalian anti-CTLA4 antibodies, humanized anti-CTLA4 antibodies, monoclonal anti-CTLA4 antibodies, polyclonal anti-CTLA4 antibodies, chimeric anti-CTLA4 antibodies, MDX-010 (ipilimumab), tremelimumab, anti-CD28 antibodies, anti-CTLA4 adnectins, anti-CTLA4 domain antibodies, single chain anti-CTLA4 fragments, heavy chain anti-CTLA4 fragments, light chain anti-CTLA4 fragments, inhibitors of CTLA4 that agonize the co-stimulatory pathway, the antibodies disclosed in PCT Publication No. WO 2001/014424, the antibodies disclosed in PCT Publication No. WO 2004/035607, the antibodies disclosed in U.S. Publication No. 2005/0201994, and the antibodies disclosed in granted European Patent No. EP 1212422 B1. Additional CTLA-4 antibodies are described in U.S. Pat. Nos. 5,811,097, 5,855,887, 6,051,227, and 6,984,720; in PCT Publication Nos. WO 01/14424 and WO 00/37504; and in U.S. Publication Nos. 2002/0039581 and 2002/086014. Other anti-CTLA-4 antibodies that can be used in a method of the present invention include, for example, those disclosed in: WO 98/42752; U.S. Pat. Nos. 6,682,736 and 6,207,156; Hurwitz et al., Proc. Natl. Acad. Sci. USA, 95(17):10067-10071 (1998); Camacho et al., J. Clin. Oncology, 22(145): Abstract No. 2505 (2004) (antibody CP-675206); Mokyr et al., Cancer Res., 58:5301-5304 (1998), and U.S. Pat. Nos. 5,977,318, 6,682,736, 7,109,003, and 7,132,281. Additional anti-CTLA4 antagonists include, but are not limited to, the following: any inhibitor that is capable of disrupting the ability of CD28 antigen to bind to its cognate ligand, to inhibit the ability of CTLA4 to bind to its cognate ligand, to augment T cell responses via the co-stimulatory pathway, to disrupt the ability of B7 to bind to CD28 and/or CTLA4, to disrupt the ability of B7 to activate the costimulatory pathway, to disrupt the ability of CD80 to bind to CD28 and/or CTLA4, to disrupt the ability of CD80 to activate the co-stimulatory pathway, to disrupt the ability of CD86 to bind to CD28 and/or CTLA4, to disrupt the ability of CD86 to activate the co-stimulatory pathway, and to disrupt the costimulatory pathway, in general from being activated. This necessarily includes small molecule inhibitors of CD28, CD80, CD86, CTLA4, among other members of the co-stimulatory pathway; antibodies directed to CD28, CD80, CD86, CTLA4, among other members of the co-stimulatory pathway; antisense molecules directed against CD28, CD80, CD86, CTLA4, among other members of the co-stimulatory pathway; adnectins directed against CD28, CD80, CD86, CTLA4, among other members of the costimulatory pathway, RNAi inhibitors (both single and double stranded) of CD28, CD80, CD86, CTLA4, among other members of the co-stimulatory pathway, among other anti-CTLA4 antagonists.

In some embodiments, the compounds of the present disclosure may be used in combination with one or more therapeutic agents that inhibit TIM-3. Blocking the activation of TIM-3 by a ligand, results in an increase in Th1 cell activation. Furthermore, TIM-3 has been identified as an important inhibitory receptor expressed by exhausted CD8+ T cells. TIM-3 has also been reported as a key regulator of nucleic acid mediated antitumor immunity. In one example, TIM-3 has been shown to be upregulated on tumor-associated dendritic cells (TADCs).

Methods of Administration

The compounds as used in the methods described herein can be administered by any suitable method and technique presently or prospectively known to those skilled in the art. For example, the active components described herein can be formulated in a physiologically- or pharmaceutically-acceptable form and administered by any suitable route known in the art including, for example, oral and parenteral routes of administering. As used herein, the term "parenteral" includes subcutaneous, intradermal, intravenous, intramuscular, intraperitoneal, and intrasternal administration, such as by injection. Administration of the active components of their compositions can be a single administration, or at continuous and distinct intervals as can be readily determined by a person skilled in the art.

Compositions, as described herein, comprising an active compound and an excipient of some sort may be useful in a variety of medical and non-medical applications. For example, pharmaceutical compositions comprising an active compound and an excipient may be useful for the treatment or prevention of an infection with a *Mycobacterium.*

"Excipients" include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture can be found, for example, in Remington's Pharmaceutical Sciences, Sixteenth Edition, E. W. Martin (Mack Publishing Co., Easton, Pa., 1980), and Remington: The Science and Practice of Pharmacy, 21st Edition (Lippincott Williams & Wilkins, 2005).

Exemplary excipients include, but are not limited to, any non-toxic, inert solid, semisolid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on what the composition is useful for. For example, with a pharmaceutical composition or cosmetic composition, the choice of the excipient will depend on the route of administration, the agent being delivered, time course of delivery of the agent, etc., and can be administered to humans and/or to animals, orally, rectally, parenterally, intracisternally, intravaginally, intranasally, intraperitoneally, topically (as by powders, creams, ointments, or drops), buccally, or as an oral or nasal spray. In some embodiments, the active compounds disclosed herein are administered topically.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxy vinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid. Other preservatives include tocopherol, tocopherol acetate, deteroxime mesylate, cetrimide, butylated hydroxyanisol (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *Litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Additionally, the composition may further comprise a polymer. Exemplary polymers contemplated herein include, but are not limited to, cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts, other polysaccharides and polysaccharide derivatives such as starch, dextran, dextran derivatives, chitosan, and alginic acid and its various salts, carageenan, various gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, albumin, and fibrin, other polymers, for example, polyhydroxyacids such as polylactide, polyglycolide, polyl(lactide-co-glycolide) and poly(.epsilon.-caprolactone-co-glycolide)-, carboxyvinyl polymers and their salts (e.g., carbomer), polyvinylpyrrolidone (PVP), polyacrylic acid and its salts, polyacrylamide, polyacrylic acid/acrylamide copolymer, polyalkylene oxides such as polyethylene oxide, polypropylene oxide, poly(ethylene oxide-propylene oxide), and a Pluronic polymer, polyoxy ethylene (polyethylene glycol), polyanhydrides, polyvinylalchol, polyethyleneamine and polypyrridine, polyethylene glycol (PEG) polymers, such as PEGylated lipids (e.g., PEG-stearate, 1,2-Distearoyl-sn-glycero-3-Phosphoethanolamine-N-[Methoxy(Polyethylene glycol)-1000], 1,2-Distearoyl-sn-glycero Phosphoethanolamine-N-[Methoxy(Polyethylene glycol)-2000], and 1,2-Distearoyl-sn-glycero-3-Phosphoethanolamine-N-[Methoxy(Polyethylene glycol)-5000]), copolymers and salts thereof.

Additionally, the composition may further comprise an emulsifying agent. Exemplary emulsifying agents include, but are not limited to, a polyethylene glycol (PEG), a polypropylene glycol, a polyvinyl alcohol, a poly-N-vinyl pyrrolidone and copolymers thereof, poloxamer nonionic surfactants, neutral water-soluble polysaccharides (e.g., dextran, Ficoll, celluloses), non-cationic poly(meth)acrylates, non-cationic polyacrylates, such as poly (meth) acrylic acid, and esters amide and hydroxy alkyl amides thereof, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxy vinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the emulsifying agent is cholesterol.

Liquid compositions include emulsions, microemulsions, solutions, suspensions, syrups, and elixirs. In addition to the active compound, the liquid composition may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable compositions, for example, injectable aqueous or oleaginous suspensions may be formulated according to the known art using suitable dispersing or wetting agents and suspending agents. The sterile injectable preparation may also be a injectable solution, suspension, or emulsion in a nontoxic parenterally acceptable diluent or solvent, for example, as a solution in 1,3-butanediol. Among the acceptable vehicles and solvents for pharmaceutical or cosmetic compositions that may be employed are water, Ringer's solution, U.S.P. and isotonic sodium chloride solution. In addition, sterile, fixed oils are conventionally employed as a solvent or suspending medium. Any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80. The injectable composition can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be in the form of suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid compositions include capsules, tablets, pills, powders, and granules. In such solid compositions, the particles are mixed with at least one excipient and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

Tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

Compositions for topical or transdermal administration include ointments, pastes, creams, lotions, gels, powders, solutions, sprays, inhalants, or patches. The active compound is admixed with an excipient and any needed preservatives or buffers as may be required.

The ointments, pastes, creams, and gels may contain, in addition to the active compound, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the active compound, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the nanoparticles in a proper medium. Absorption enhancers can also be used to increase the flux of the compound across the skin. The rate can be controlled by either providing a rate controlling membrane or by dispersing the particles in a polymer matrix or gel.

The active ingredient may be administered in such amounts, time, and route deemed necessary in order to achieve the desired result. The exact amount of the active ingredient will vary from subject to subject, depending on the species, age, and general condition of the subject, the severity of the infection, the particular active ingredient, its mode of administration, its mode of activity, and the like. The active ingredient, whether the active compound itself, or the active compound in combination with an agent, is preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

The active ingredient may be administered by any route. In some embodiments, the active ingredient is administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. In general, the most appropriate route of administration will depend upon a variety of factors including the nature of the active ingredient (e.g., its stability in the environment of the gastrointestinal tract), the condition of the subject (e.g., whether the subject is able to tolerate oral administration), etc.

The exact amount of an active ingredient required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

Useful dosages of the active agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

A number of embodiments of the disclosure have been described. Nevertheless, it will be understood that various modifications may be made without departing from the spirit and scope of the invention. Accordingly, other embodiments are within the scope of the following claims.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric pressure. There are numerous variations and combinations of reaction conditions, e.g. component concentrations, temperatures, pressures, and other reaction ranges and conditions that can be used to optimize the product purity and yield obtained from the described process. Only reasonable and routine experimentation will be required to optimize such process conditions.

Representative compounds of the present disclosure may be prepared using the process provided in the following scheme showing the synthesis of UR238:

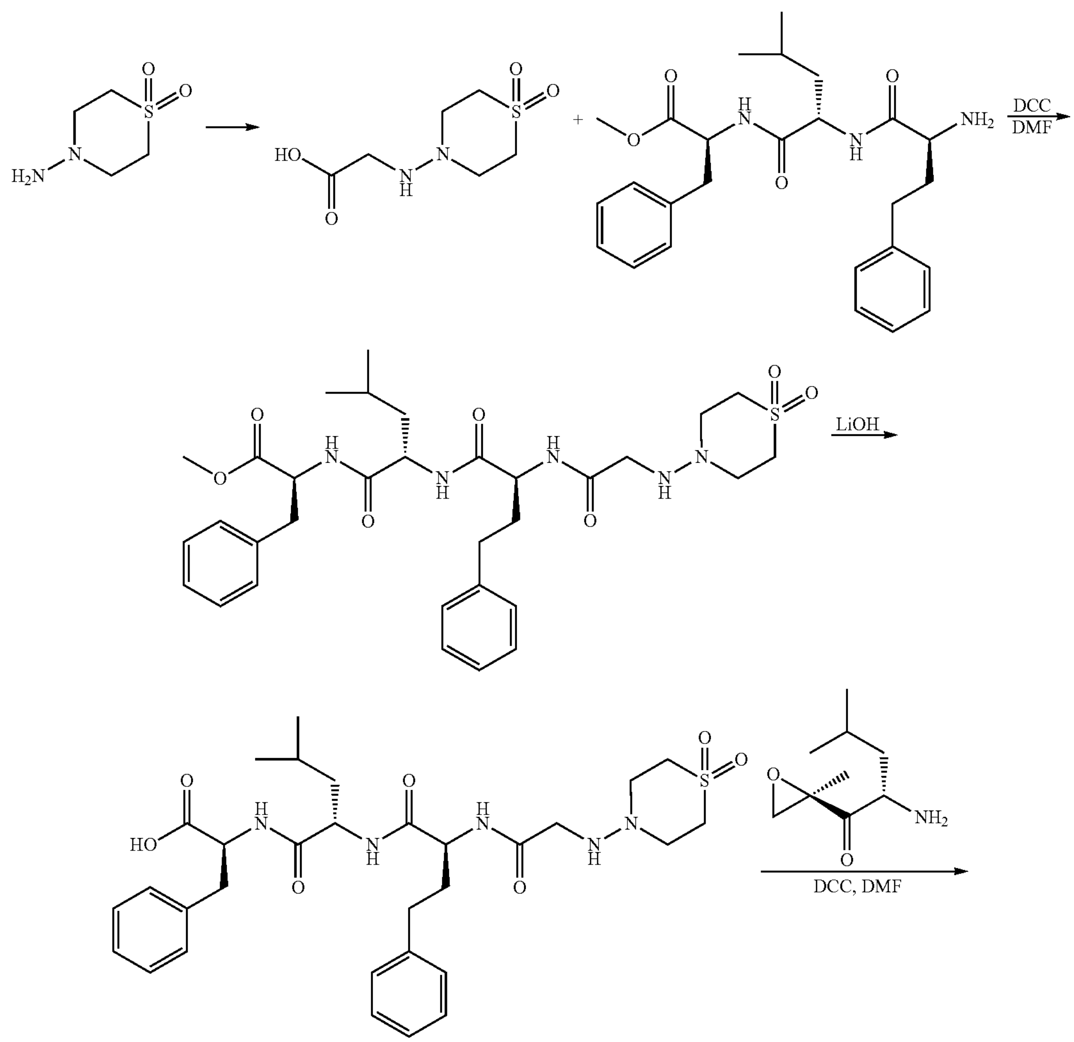

-continued

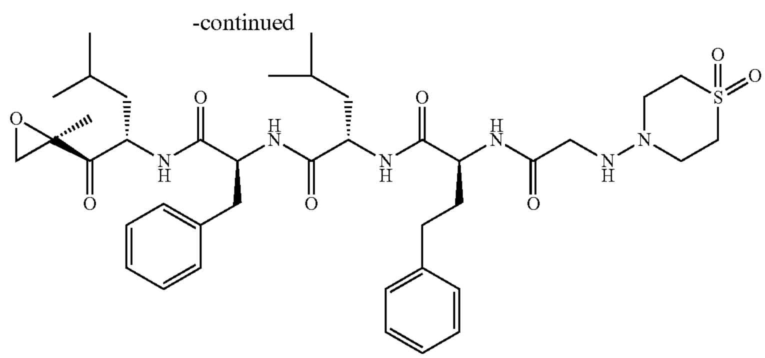

UR238 Inhibited HE4 Expression in SKOV-3 Ovarian Cancer Cells

HE4 expression in SKOV-3 ovarian cancer cells was analyzed following treatment with DMSO or UR238 (0.5 or 2 μM). GAPDH expression was analyzed as a control. The results are found in FIG. 1. HE4 expression was found to be inhibited in UR238 treated cells compared to DMSO treated cells.

UR238 Inhibited HE4 Secretion from ECC-1 Endometrial Cancer Cells

Figure 2:
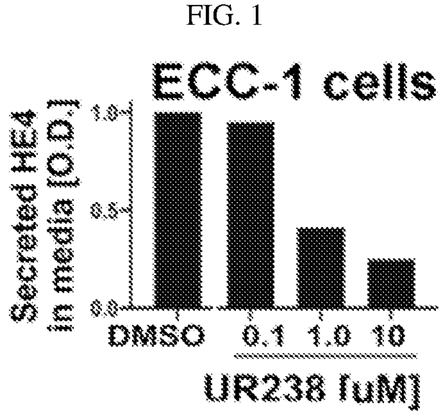
FIG. 2 shows secreted HE4 levels in media of ECC-1 endometrial cancer cells treated with DMSO or UR238 (0.1, 1.0, or 10 μM). UR238 inhibited HE4 secretion from ECC-1 cells.

HE4 secretion from ECC-1 endometrial cancer cells was analyzed. The cells were treated with either DMSO or UR238 at 0.1, 1.0, or 10 μM concentration. The results are found in FIG. 2. Secreted HE4 levels were found to be decreased for cells treated with UR238 compared to DMSO treated cells.

UR238 Inhibited Growth of an Ovarian Cancel Cell Derived Xenograft in NSG Mice

Figure 3:
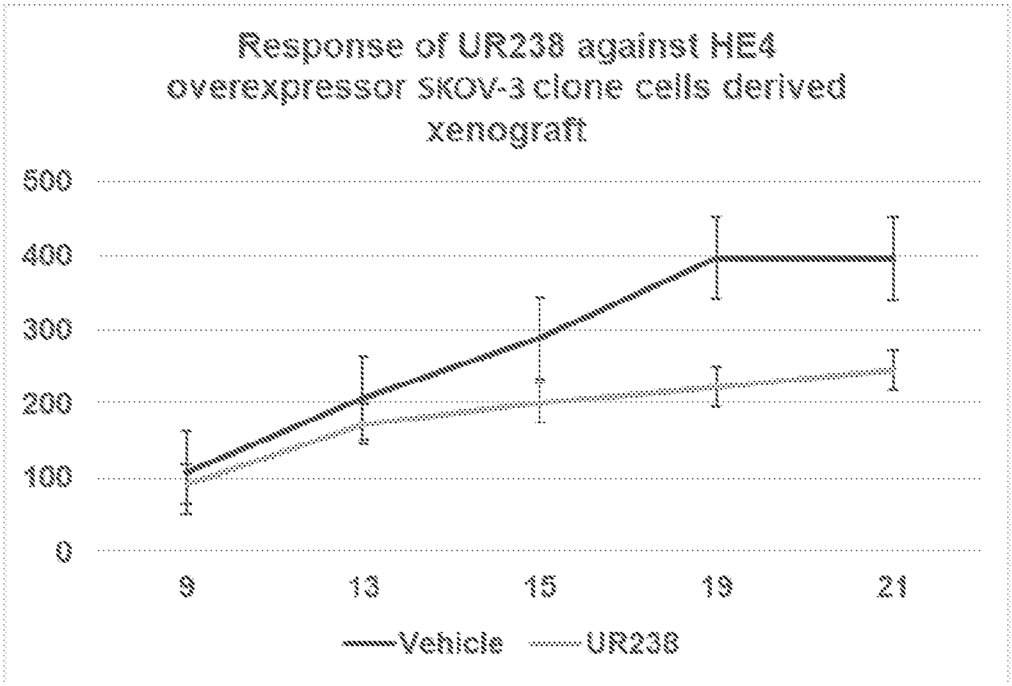
FIG. 3 shows tumor volumes ($mm^3$) of SKOV-3SH1 ovarian cancer cell derived xenografts in NSG mice treated with vehicle or UR238 over cited monitoring days. UR238 inhibited growth of the ovarian cancer cell derived xenograft.

The effect of UR238 treatment on SKV-3 SH1 ovarian cancer cell derived xenografts in NSG mice was analyzed. Treatment with vehicle or UR238 started at 9 days post implantation, and tumor size was measured at 9, 13, 15, 18, and 21 days post implantation. The results are found in FIG. 3. UR238 treatment inhibited growth of the SKOV-3 cancer cell derived xenografts.

Figure 4:
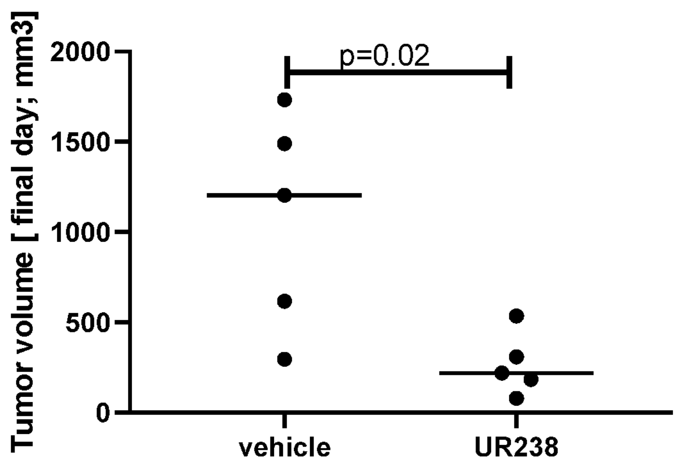
FIG. 4 shows tumor volumes ($mm^3$) of AN3CA endometrial cancer cell derived xenografts in NSG mice treated with vehicle or UR238 over cited monitoring days. Ur238 inhibited growth of the endometrial cancer cell derived xenograft.
Figure 5:
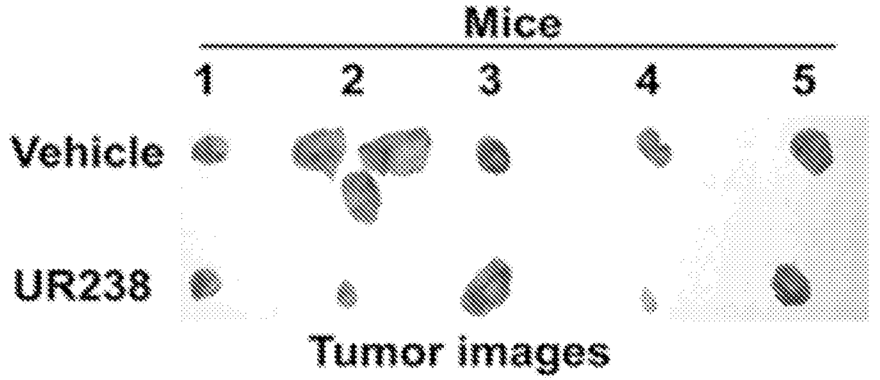
FIG. 5 shows images of the AN3CA cell derived xenograft tumors treated with vehicle or UR238 in mice.

UR238 Inhibited Growth of an Endometrial Cancer Cell Derived Xenograft in NSF Mice The effect of UR238 treatment of AN3CA endometrial cancer cell derived xenografts in NSG mice was analyzed. Treatment with vehicle or UR238 started at 9 days post implantation, and tumor size was measured at 10, 14, 18, and 21 days post implantation. The results are found in FIG. 4 and images of the excised tumors are found in FIG. 5. UR238 treatment inhibited growth of the AN3CA cancer cell derived xenografts.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A compound selected from:

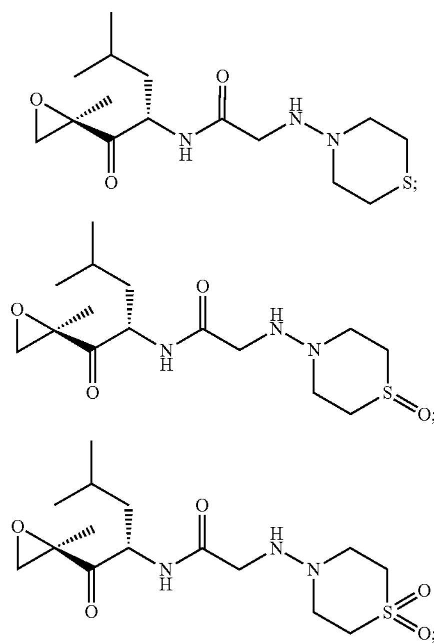

-continued

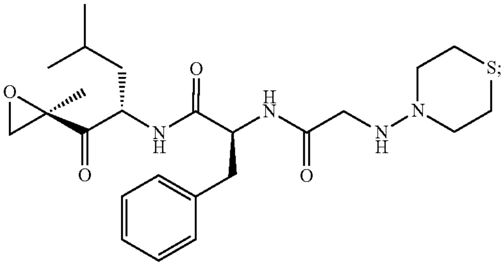

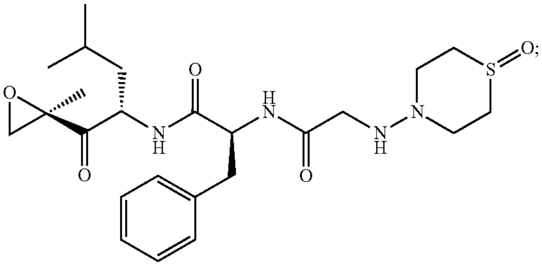

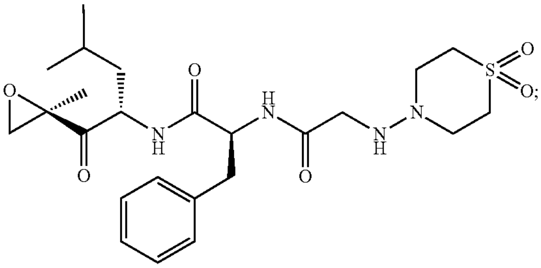

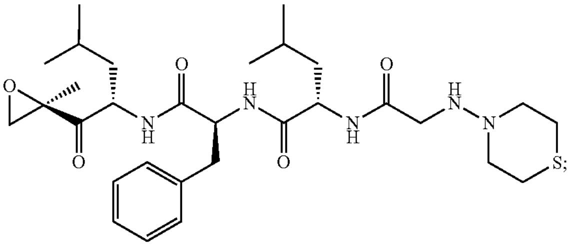

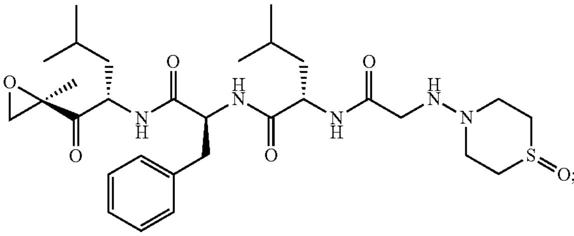

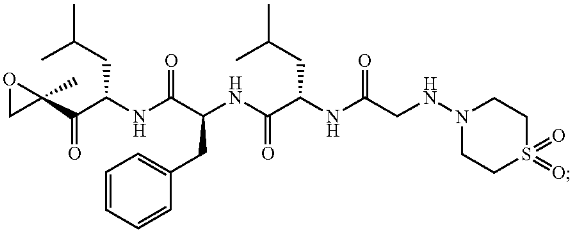

-continued

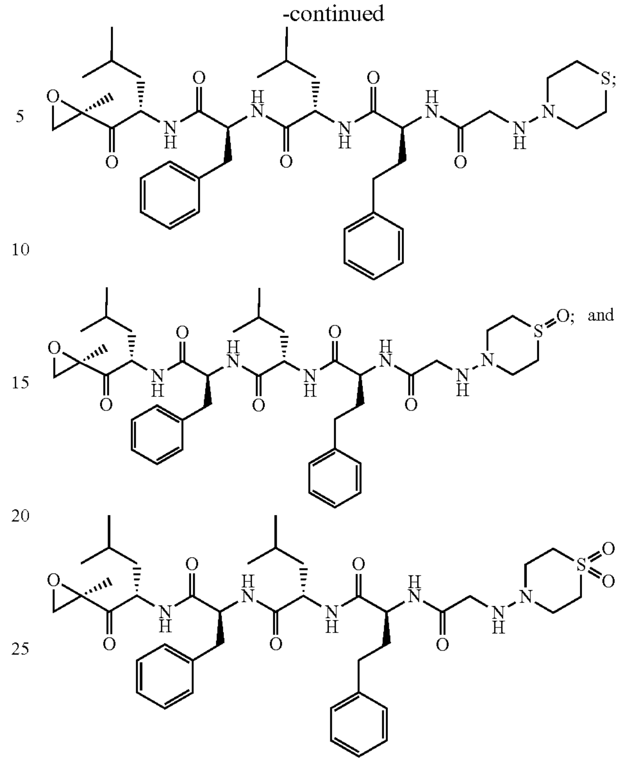

and or a pharmaceutically acceptable salt or derivative thereof.

2. A pharmaceutical composition comprising a compound of claim 1, or a pharmaceutically acceptable salt or derivative thereof, in a pharmaceutically acceptable carrier.

3. A method of treating cancer in a subject in need thereof comprising administering a therapeutically effective amount of a compound of claim 1, or a pharmaceutically acceptable salt or derivative thereof.

4. The method of claim 3, wherein the cancer is selected from a carcinoma or sarcoma, or wherein the cancer is selected from ovarian cancer, endometrial cancer, breast cancer, lung cancer, or testicular cancer.

5. The method of claim 3, wherein the cancer is a refractory cancer or an immunogenic cancer.

6. The method of claim 5, wherein the immunogenic cancer is selected from malignant melanoma and renal cell carcinoma, Mantel cell lymphoma, follicular lymphoma, diffuse large B-cell lymphoma, T-cell acute lymphoblastic leukemia, Burkitt Lymphoma, myeloma, immunocytoma, acute promyelocyte leukemia, chronic myeloid/acute lymphoblastic leukemia, acute leukemia, B-cell acute lymphoblastic leukemia, anaplastic large cell leukemia, myelodysplasia syndrome/acute myeloid leukemia, non-Hodgkin's lymphoma, chronic lymphocytic leukemia, acute myelogenous leukemia(AML), common (pre-B)acute lymphocytic leukemia, malignant melanoma, T-cell lymphoma, leukemia, B-cell lymphoma, epithelial malignancies, lymphoid malignancies, gynecologic carcinoma, biliary adenocarcinomas and ductal adenocarcinomas of the pancreas.

7. A method of treating an inflammatory disorder, organ fibrosis, or infertility in a subject in need thereof comprising administering a therapeutically effective amount of a compound of claim 1, or a pharmaceutically acceptable salt or derivative thereof.

8. The method of claim 7, wherein the organ fibrosis is selected from renal fibrosis, pulmonary fibrosis, cirrhosis, endomyocardial fibrosis, Crohn's disease, liver fibrosis, heart fibrosis, scleroderma, or progressive massive fibrosis.
9. The compound of claim 1, wherein the compound is
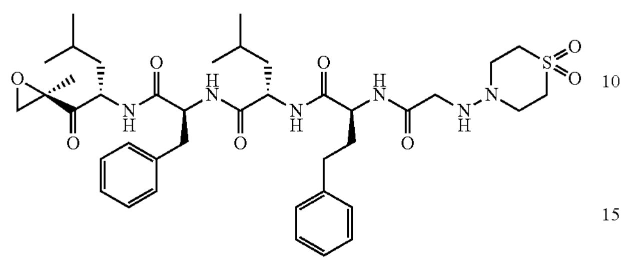
or a pharmaceutically acceptable salt or derivative thereof.
* * * * *